US012729387B2

(12) United States Patent
Bruhlmann et al.

(10) Patent No.: US 12,729,387 B2
(45) Date of Patent: Sep. 8, 2026

(54) PROCESS FOR MAKING FLAVOR AND FRAGRANT COMPOUNDS

(71) Applicant: Firmenich SA, Satigny (CH)

(72) Inventors: Fredi Bruhlmann, Geneva (CH); Rebecca Buller, Wadenswil (CH)

(73) Assignee: Firmenich SA, Satigny (CH)

( * ) Notice: Subject to any disclaimer, the term of this patent is extended or adjusted under 35 U.S.C. 154(b) by 5 days.

(21) Appl. No.: 18/587,305

(22) Filed: Feb. 26, 2024

(65) Prior Publication Data

US 2024/0191261 A1 Jun. 13, 2024

Related U.S. Application Data

(63) Continuation of application No. 17/165,922, filed on Feb. 2, 2021, which is a continuation of application No. 15/547,563, filed as application No. PCT/US2016/016471 on Feb. 3, 2016, now Pat. No. 10,941,419.

(30) Foreign Application Priority Data

Feb. 3, 2015 (WO) ................. PCT/EP2015/052174

(51) Int. Cl.

| | |
|---|---|
| ***C12P 7/04*** | (2006.01) |
| ***C07B 31/00*** | (2006.01) |
| ***C11B 9/00*** | (2006.01) |
| ***C12N 9/02*** | (2006.01) |
| ***C12N 9/88*** | (2006.01) |
| ***C12P 7/24*** | (2006.01) |

(52) U.S. Cl.

CPC ................ *C12P 7/04* (2013.01); *C07B 31/00* (2013.01); *C11B 9/0015* (2013.01); *C12N 9/004* (2013.01); *C12N 9/88* (2013.01); *C12P 7/24* (2013.01)

(58) Field of Classification Search

CPC .... C12P 7/04; C12P 7/24; C07B 31/00; C11B 9/0015; C12N 9/004; C12N 9/88

See application file for complete search history.

(56) References Cited

U.S. PATENT DOCUMENTS

| | | | |
|---|---|---|---|
| 5,464,761 | A | 11/1995 | Muller et al. |
| 5,695,973 | A | 12/1997 | Subbiah |
| 7,037,693 | B2 | 5/2006 | Brash et al. |
| 8,501,452 | B2 | 8/2013 | Bruhlmann et al. |
| 2002/0098570 | A1 | 7/2002 | Brash et al. |
| 2005/0204437 | A1 | 9/2005 | Breddam et al. |
| 2010/0203586 | A1 | 8/2010 | Bruhlmann et al. |

FOREIGN PATENT DOCUMENTS

| | | | |
|---|---|---|---|
| EP | 0801133 | A2 | 10/1997 |
| WO | 9526413 | A1 | 10/1995 |
| WO | 0194606 | A2 | 12/2001 |

OTHER PUBLICATIONS

Hatanaka et al. (Biosynthetic pathway of cucumber alcohol: trans-2,Cis-6 nonadienol via Cis-3,Cis-6- nonadienal. (1975), 14: 2589-2592) . (Year: 1975).*

Hatanaka et al., "Biosynthetic Pathway for C6-Aldehydes Formation From Linolenic Acid in Green Leaves", Chemistry and Physics of Lipids, 1987, pp. 341-361, 44(2-4).

Hatanaka, "The Biogeneration of Green Odour by Green Leaves", Phytochemistry, 1993, pp. 1201-1218, 34(5).

Hatanaka et al., "The Biogeneration of Green Odour by Green Leaves and It's Physiological Functions—Past, Present and Future", Zeitschrift für Naturforschung C, 1995, pp. 467-472, 50(7-8).

Tijet et al., "Purification, Molecular Cloning, and Expression of the Gene Encoding Fatty Acid 13-Hydroperoxide Lyase from Guava Fruit (*Psidium guajava*)", Lipids, 2000, pp. 709-720, 35(7).

Tijet et al., "Biogenesis of Volatile Aldehydes from Fatty Acid Hydroperoxides: Molecular Cloning of a Hydroperoxide Lyase (CYP74C) with Specificity for both the 9- and 13-Hydroperoxides of Linoleic and Linolenic Acids", Archives of Biochemistry and Biophysics, 2001, pp. 281-289, 386(2).

International Search Report for PCT/US16/16471 issued on Apr. 15, 2016, 3 pages.

* cited by examiner

*Primary Examiner* — Iqbal H Chowdhury

(74) *Attorney, Agent, or Firm* — Clark & Elbing LLP

(57) ABSTRACT

Described herein are methods of producing hexenols including: a) contacting a hydroperoxide of a polyunsaturated fatty acid with a modified hydroperoxide lyase to form a hexenal; and b) reducing the hexenal to a hexenol in the presence of a hydride donor, a ketoreductase, and a co-factor, where the contacting and reducing steps are carried out at essentially the same time in the substantial absence of baker's yeast.

5 Claims, 3 Drawing Sheets

PROCESS FOR MAKING FLAVOR AND FRAGRANT COMPOUNDS

RELATED APPLICATIONS

Figure 1A:
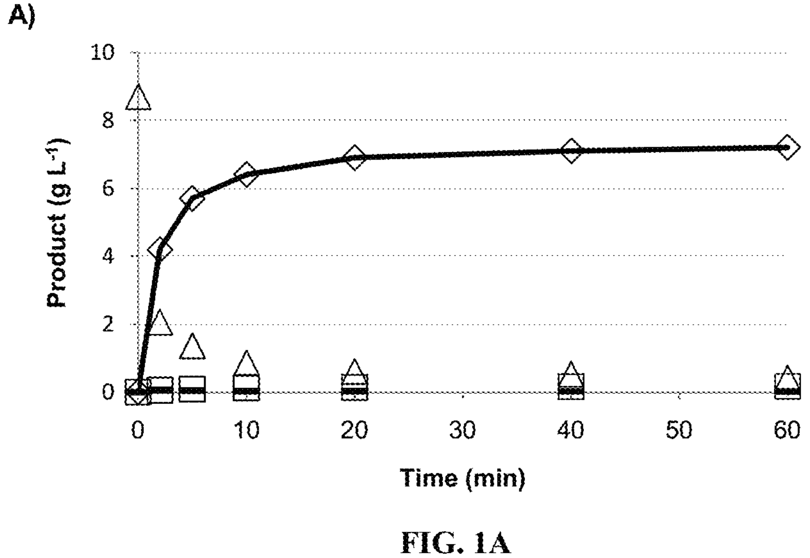

This application is a continuation application of U.S. application Ser. No. 17/165,922, filed Feb. 2, 2021, which is a divisional application of U.S. application Ser. No. 15/547,563, filed Jul. 31, 2017, which is a national stage application under 35 U.S.C. § 371 filing of International Patent Application PCT/US2016/016471, filed Feb. 3, 2016, which claims the benefit of International Patent Application PCT/EP2015/052174, filed Feb. 3, 2015, each of which is hereby incorporated by reference in its entirety.

FIELD OF THE INVENTION

The field is processes for making flavors and fragrances

BACKGROUND

Among the compounds which are useful in the perfume and flavor industry, involving hydroperoxide cleavage possibly carried out via enzymatic reaction, the so called "green notes" include n-hexanal, n-hexanol, (E)-2-hexenal, (E)-2-hexen-1-ol, (Z)-3-hexen-1-ol (also known as pipol) and (Z)-3-hexen-1-al, which are widely used in fragrances and flavors, particularly fruit flavors, to impart a fresh green character. Furthermore, green notes are essential for fruit aroma and are used extensively in the aroma industry. The demand for natural green notes has grown to exceed their supply from traditional sources such as mint (*Mentha arvensis*) oil. This has motivated research efforts toward finding alternative natural ways of obtaining these materials.

The synthesis of green note compounds starts from free (polyunsaturated) fatty acids such as linoleic (9-(Z),12-(Z)-octadecadienoic) and α-linolenic (9-(Z),12-(Z),15-(Z)-octadecatrienoic) acids. In nature, these acids are released from cell membranes by lipolytic enzymes after cell damage. Fatty acid 13-hydroperoxides are formed by the action of a specific 13-lipoxygenase (13-LOX) and are subsequently cleaved by a specific 13-hydroperoxide lyase (13-HPL) into a $C_6$ aldehyde and a $C_{12}$ ω-oxoacid moiety. The aldehydes can subsequently undergo thermal isomerization and/or be reduced by dehydrogenase enzymes to produce other $C_6$ products (i.e. green notes) such as alcohols and esters (Hatanaka A. (1993) Phytochemistry 34: 1201-1218; Hatanaka A. et al. (1987) Chemistry and Physics of Lipids 44: 431-361).

Guava has been identified as an excellent source of freeze-stable 13-HPL for use in this synthetic pathway. Guava 13-HPL is described for use in an industrial process for the production of green notes (U.S. Pat. No. 5,464,761). In this process, a solution of the required 13-hydroperoxides is made from linoleic or α-linolenic acid (obtained from sunflower and linseed oils, respectively) using freshly prepared soybean flour as a source of 13-LOX. This solution is then mixed with a freshly prepared puree of whole guava (*Psidium guajava*) fruit as the source for 13-HPL. The aldehyde products are then isolated by distillation. When the corresponding alcohols are required, fresh baker's yeast is added to the hydroperoxide solution before it is mixed with the guava puree. The yeast contains an active alcohol dehydrogenase enzyme that reduces the aldehydes to the corresponding alcohols as the aldehydes are formed by 13-HPL.

SUMMARY OF THE INVENTION

Provided herein is a method of producing an alcohol comprising: a) contacting a hydroperoxide of a polyunsaturated fatty acid with a hydroperoxide lyase to form an aldehyde; and b) reducing the aldehyde in the presence of a hydride donor, a ketoreductase, and a co-factor to form an alcohol, wherein the contacting and reducing steps are carried out at essentially the same time.

Further provided herein is a composition comprising (Z)-3-hexenol wherein the composition comprises (Z)-3-hexenol in an amount of about greater than or equal to 12000 mg/L and is further provided with about less than or equal to 400 mg/L of the total amount of n-hexanal, (Z)-3-hexenal, (E)-2-hexenal, (E)-2-hexenol, and n-hexanol produced in the reaction wherein the n-hexanal, (Z)-3-hexenal, (E)-2-hexenal, (E)-2-hexenol, and n-hexanol have not been removed after processing.

Further provided herein is a composition comprising (Z,Z)-3,6-nonadienol wherein the composition comprises (Z,Z)-3,6-nonadienol in an amount greater than or equal to about 0.74 g/l, more particularly greater than or equal to about 1.8 g/l, even more particularly greater or equal to about 2 g/l and wherein the composition may comprise about less than or equal to about 1 g/1 L (Z)-3-nonenol, more particularly about less than or equal to 0.2 g/l and even more particularly less than or equal to about 0.16 g/l, In one embodiment, the composition comprises no (Z)-3-nonenol.

DETAILED DESCRIPTION OF THE DRAWINGS

FIG. 1A: shows sequential cleavage and reduction involving the modified 13-HPL (variant GC7) and the ketoreductase ADH005. Note that the cleavage reaction had already proceeded for 5 min prior to the addition of the ketoreductase, isopropanol and co-factor at t=0 min. The following symbols apply in the graph: (Z)-3-hexenol (diamond), (E)-2-hexenol (squares), (Z)-3-hexenal (triangle), (E)-2-hexenal (horizontal bar).

Figure 1B:
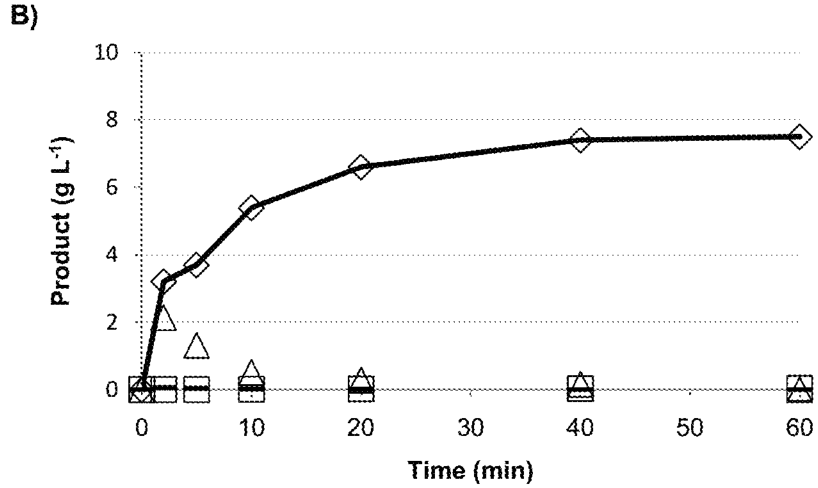

FIG. 1B: shows concomitant cleavage and reduction involving the modified 13-HPL (variant GC7) and the ketoreductase ADH005. The following symbols apply in the graph: (Z)-3-hexenol (diamond), (E)-2-hexenol (squares), (Z)-3-hexenal (triangle), (E)-2-hexenal (horizontal bar).

Figure 2:
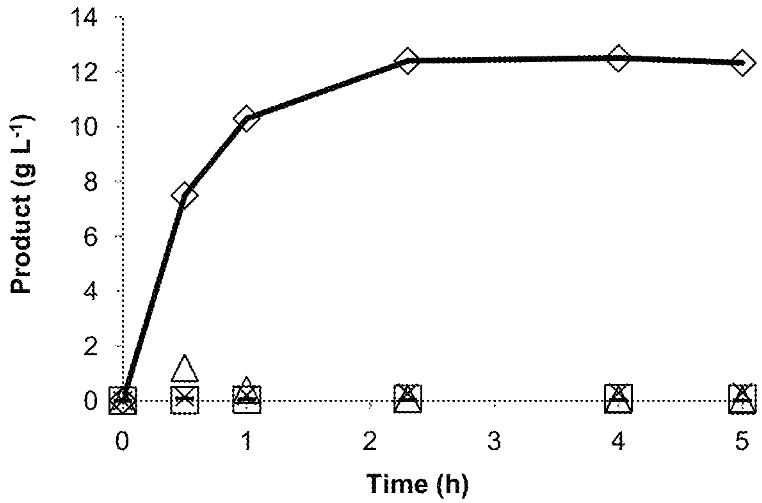

FIG. 2: shows the concomitant cleavage and reduction involving the modified 13-HPL variant GC7 and the ketoreductase IEPox58. The following symbols apply in the graph: (Z)-3-hexenol (diamond), (E)-2-hexenol (square), (Z)-3-hexenal (triangle), (E)-2-hexenal (horizontal bar), and n-hexanol (star).

Figure 3:
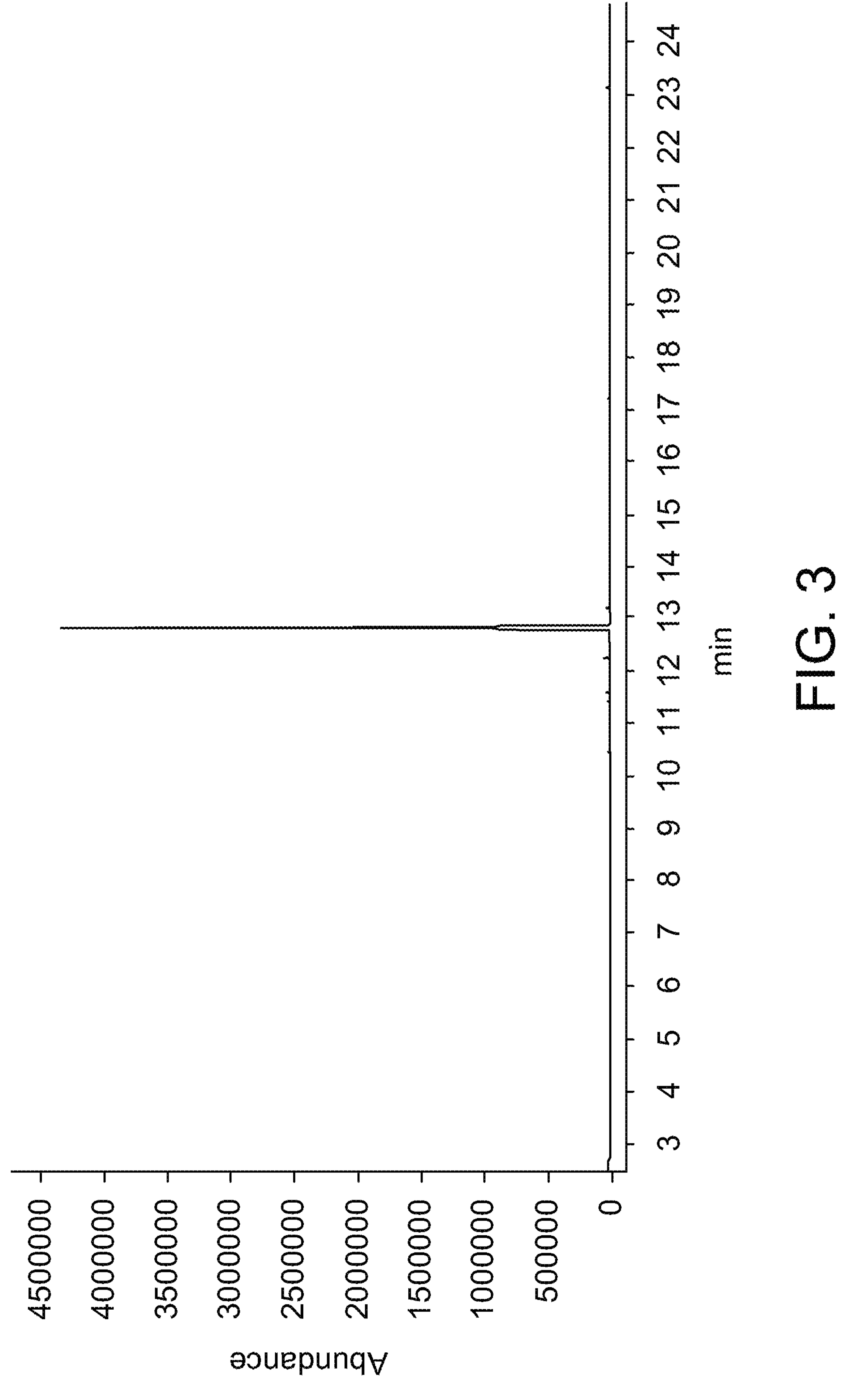

FIG. 3: shows the gas chromatogram of isolated (Z)-3-hexenol

DETAILED DESCRIPTION

In one embodiment, the hydroperoxide of the polyunsaturated fatty acid provided herein is selected from a 9-hydroperoxide of polyunsaturated acid and a 13-hydroperoxide of a polyunsaturated fatty acid.

In one embodiment, the aldehyde is a $C_6$ aldehyde.

In one embodiment the $C_6$ aldehyde a hexanal, particularly a n-hexanal.

In one embodiment the $C_6$ aldehyde is selected from the group consisting of n-hexanal, (E)-2-hexenal, and (Z)-3-hexenal, particularly (Z)-3-hexenal.

In one embodiment, the aldehyde is selected from the group consisting of nonenal and nonadienal.

In one embodiment the aldehyde is selected from the group consisting of (Z)-3-nonenal and (Z,Z)-3,6-nonadienal.

In yet another embodiment, the alcohol is a $C_6$ alcohol selected from the group consisting n-hexanol, (E)-2-hexenol, and (Z)-3-hexenol, particularly (Z)-3-hexenol.

In yet another embodiment, the alcohol is a $C_9$ alcohol.

In yet another embodiment, the alcohol is a $C_9$ alcohol selected from the group consisting (Z)-3-nonenol and (Z,Z)-3,6-nonadienol, particularly (Z,Z)-3,6-nonadienol. In one embodiment, the ratio (Z)-3-hexenol to the total amount of n-hexanal, (Z)-3-hexenal, (E)-2-hexenal, (E)-2-hexenol, and n-hexanol ranges, by weight, from about 30:1 up to at least about 71:1, more particularly from about 30:1 to about 71:1. In one embodiment, the ratio of (Z,Z)-3,6-nonadienol to (Z)-3-nonenol ranges from about 4.63 up to about 25:1.

In one embodiment, the hydride donor is a compound that donates a hydride of a compound selected from the group consisting of a secondary alcohol, a primary alcohol, an alkandiol and a hydroxy acid or one of its esters.

In one embodiment, the secondary alcohol is selected from the group consisting of isopropanol, isoamyl alcohol, glycerol, isobutanol, butan-2-ol, propylene glycol, fenchol, borneol, menthol, carveol, methyl-p-tolyl-carbinol, 8-cymenol, oct-1-en-3-ol, pentan-2-ol, pentan-3-ol, 4-methyl-2-pentanol, hexan-2-ol, heptan-2-ol, octan-2-ol, nonan-2-ol, decan-2-ol, undecan-2-ol In a particular embodiment the hydride donor is isopropranol.

In one embodiment, the hydride donor is an alkandiol selected from the group consisting of, butan-1,4-diol, butan-2,3-diol and ethylene glycol.

In another embodiment, the hydride donor is a hydroxy acid esters selected from the group consisting of particularly calcium lactate, ethyl lactate, propyl lactate and butyl lactate.

In one embodiment, the hydroperoxide lyase is a modified lyase produced in a modified organism harboring a recombinant expression plasmid with the modified 13-hpl gene (particular *E. coli* organism, variant GC7) described e.g. in U.S. Pat. No. 8,501,452 (B2) the entirety of which is incorporated herein by reference.

In one embodiment, the hydroperoxide lyase is a modified lyase generated by a modified organism harboring a recombinant expression plasmid with a modified 9-hydroperoxide lyase, which is used for producing $C_9$ aldehydes and after their reduction the $C_9$ alcohols particularly (Z)-3-nonenol (if 9-hydroperoxide of linoleic acid (9-HPOD) is used as the substrate), or (Z,Z)-3,6-nonadienol (if 9-hydroperoxide of alpha-linolenic acid (9-HPOT) is used as the substrate). From the alcohols the corresponding acetate or other esters may be produced. Particularly, the lyase is generated from an organism harboring a 9-hydroperoxide lyase gene such as described in US Patent Application Publication No.: US2002098570 (A1), the entirety of which is incorporated herein by reference.

The hydroperoxide lyases are preferably stable in presence of the hydride donor. This is surprising as alcohols for example are known in many cases to destabilize enzymes. The inventors have found that said hydroperoxide lyases are stable in the presence of certain hydride donors that allow for the concommitment hydroperoxide cleavage and aldehyde reduction.

In one embodiment the ketoreductase is selected from the group consisting of the enzyme ADH005 from Codexis (Redwood City, California) and IEPOx58 of Cambrex-IEP (Wiesbaden, Germany).

In one embodiment, the 9- and 13-hydroperoxide fatty acid is selected from the group consisting of linoleic acid and alpha-linolenic acid.

In one embodiment, the co-factor is selected from the group consisting of NADH and NADPH.

In one embodiment the co-factor regenerating enzyme may be selected from the group consisting of glucose dehydrogenase with glucose as the co-substrate, formiate dehydrogenase with formiate as the co-substrate, or phosphite dehydrogenase with phosphite as the co-substrate.

One embodiment provided herein is a composition comprising (Z)-3-hexenol wherein the composition comprises (Z)-3-hexenol in an amount of about greater than or equal to 12000 mg/L and is further provided with about less than or equal to about 400 mg/L, more particularly less than about 170 mg/L of total amount of n-hexanal, (Z)-3-hexenal, (E)-2-hexenal, (E)-2-hexenol, and n-hexanol wherein the n-hexanal, (Z)-3-hexenal, (E)-2-hexenal, (E)-2-hexenol, and n-hexanol have not been removed after processing. In another embodiments provided the composition comprises (Z)-3-hexenol in an amount of about greater than or equal to 12000 mg/L and is further provided with about less than or equal 170 up to about 400 mg/L of the total amount of n-hexanal, (Z)-3-hexenal, (E)-2-hexenal, (E)-2-hexenol and n-hexanol wherein the n-hexanal, (Z)-3-hexenal, (E)-2-hexenal, (E)-2-hexenol, and n-hexanol have not been removed after processing.

In one embodiment, the contacting and reducing steps are carried out at a temperature that ranges from about 0° C. to about 30° C., more particularly form about 10° C. to about 30° C. at a time that ranges from about 2 minutes up to about 480 minutes. In one particular embodiment the temperature is about 20° C. for a time of about 430 minutes. In another particular embodiment, the temperature is about room temperature for a time of about 5 hours. Typically the contacting and reducing steps are carried out with mixing.

The compounds provided herein are oxygen-containing compounds of current use in the flavor and fragrance industry, namely as a result of their fruity and green type organoleptic characters. There are many studies described in the literature related to a variety of synthetic methods for preparing these compounds, which are known to be constituents of several flavors and fragrances of natural origin.

One benefit of the current process is that it does not require an intact organism.

EXAMPLES

The following examples are provided for illustrative purposes only.

Example 1

13-HPOT/D Synthesis

To a 5-necked glass flask equipped with a mechanical stirrer, a thermometer, a dropping funnel, a glass cap and an oxygen inlet, the mixture of 44 g of linseed oil hydrolysate (ca. 65% of oxidizable acids) and 247.5 g of tap water were added under stirring at 240 rpm. The temperature was adjusted to 18° C. with an ice-water bath. The reaction pH was set by adding 13.2 g of an aqueous solution of 30% of NaOH. The overhead gas phase was purged three times with pure oxygen 02. The glass cap was then quickly replaced with a pH electrode. Then 38.5 g of freshly ground soy flour were added via a flask connected with a flexible hose. The stirring speed was increased to 1000-1200 rpm. The pH was kept constant at pH 9.2 to 9.4 by the drop-wise addition of an aqueous solution of 30% of NaOH. The temperature was maintained between 18-22° C. The reaction was left for one hour. The fatty acid hydroperoxide concentration was determined by iodometric titration with a 0.01 N solution of $Na_2S_2O_3$. The quality of the fatty acid hydroperoxide was controlled by HPLC. Total fatty acid hydroperoxide as determined by titration reached at least 80 g $L^{-1}$ of 13-HPOT/D (13-hydroperoxy-trienoic acid/13-hydroperoxy-dienoic acid).

Example 2

Production of the 13-Hydroperoxide Lyase (13-HPL)

0.5 mL of an overnight culture of cells of *E. coli* harboring a recombinant expression plasmid with the modified 13-hpl gene* was added to a flask with 100 mL of LB medium containing 100 mg $mL^{-1}$ of ampicillin and 2 mg $L^{-1}$ of thiamine. The culture was grown at 37° C. under shaking at 180 rpm till an optical density of $OD_{600}$=0.45 was reached. Then 5-amino-levulinic acid was added to a final concentration of 1 mM. The temperature was lowered to 25° C. within 30 minutes. The culture was induced with 0.1 mM of IPTG at an optical density of $OD_{600}$=0.6 and left at 25° C. under shaking for 18 hours. Cells of *E. coli* were then centrifuged and re-suspended in 100 mM phosphate buffer pH 7.6 to give an $OD_{600}$ of 10 prior to sonication using the Labsonic P of Sartorius (Göttingen, Germany).

* variant GC7, described e.g. in U.S. Pat. No. 8,501,452 (B2)

Example 3

Sequential Cleavage of 13-HPOT/D and Reduction of (Z)-3-Hexenal

Cleavage of crude 13-HPOT/D was carried out with lysed *E. coli* cells producing the modified 13-HPL variant GC #7. Into a 10-mL-vial were added: 1.8 mL of 13-HPOT/D >80 g $L^{-1}$ and 0.2 mL of lysed cells of *E. coli* (cell suspension equivalent to $OD_{600}$=10) containing the 13-HPL. After 5 min 400 μL of isopropanol, 25 μL of NADP (50 mM), and 120 μL of the enzyme ADH005 (775 U $mL^{-1}$) of Codexis (Redwood City, California) were added under stirring. Samples of 100 μL were withdrawn from the reaction after 2 min, 5 min, 10 min, 20 min, 40 min, 60 min, and immediately diluted with 900 μL of water. Extraction was with 1 volume of ethyl acetate containing 1 g $L^{-1}$ of n-octanol as the internal standard for analysis by gas chromatography. A gas chromatograph equipped with a flame ionization detector and a DB-WAX column (L=30 m, ID=0.25 mm, coating=0.25 μm) was used following the temperature program: 80° C. (2 min), 160° C. (4° C. $min^{-1}$), 230° C. (30° C. $min^{-1}$), 230° C. (6 min). The helium flux was 1.4 mL $min^{-1}$ using a split ratio of 1:50. After 1 hour the reaction broth contained 7.2 g $L^{-1}$ of (Z)-3-hexenol, 0.42 g $L^{-1}$ of (Z)-3-hexenal, 0.17 g $L^{-1}$ of (E)-2-hexenol, and 0.02 g $L^{-1}$ of (E)-2-hexenal. The kinetics of the reaction is shown in FIG. 1A. As shown in FIG. 1A, the ketoreductase and the co-factor NADP remained sufficiently stable under reaction conditions.

Example 4 a) Concomitant Cleavage of 13-HPOT/D and Reduction of (Z)-3-Hexenal

Into a 10-mL-vial were added: 1800 μL of 13-HPOT/D of 80 g $L^{-1}$, 4 μL of 1 M $MgSO_4$, 25 μL of 50 mm NADP, 400 μL of isopropanol, 120 μL of the ketoreductase ADH005 (775 U $mL^{-1}$) of Codexis (Redwood City, California), and 250 μL of an *E. coli* lysate (cell suspension equivalent to $OD_{600}$=10) containing the 13-HPL (variant GC #7). The reaction was stirred at room temperature. Samples of 100 μL were withdrawn from the reaction at fixed time points during one hour, diluted with 900 μL of $H_2O$ and extracted with 1 mL of ethyl acetate prior to analysis by gas chromatography as described in the previous example. n-Octanol served as the internal standard. After 1 hour the reaction broth contained 7.5 g $L^{-1}$ of (Z)-3-hexenol, 0.04 g $L^{-1}$ of (E)-2-hexenol. No aldehydes were detected. The kinetics of the reaction is shown in FIG. 1B.

b) Concomitant Cleavage of 13-HPOT/D and Reduction of (Z)-3-Hexenal

Into a 10-mL-glass-vial were added: 0.9 mL of 13-HPOT/D of 80 g $L^{-1}$, 10 μL of NAD stock solution of 5.2 mM, 200 μL of isopropanol, 23 μL of the ketoreductase IEPOx58 of Cambrex-IEP (Wiesbaden, Germany) and 200 μL of the 13-HPL variant GC7 lysate (made of a cell suspension of $OD_{600}$=10). The reaction was stirred with a magnetic bar at 400 rpm at 10° C. for up to 5 hours. The reaction was extracted with 3 volumes of MTBE for analysis by GC using n-octanol as the internal standard. After 5 hour the reaction broth contained 12.3 g $L^{-1}$ of (Z)-3-hexenol, 0.02 g $L^{-1}$ of (Z)-3-hexenal, 0.07 g $L^{-1}$ of (E)-2-hexenol, 0.01 g $L^{-1}$ of (E)-2-hexenal, 0.3 g $L^{-1}$ of 1-hexanol. The kinetics of the reaction is shown in FIG. 2.

Example 5

Preparation of (Z)-3-Hexenol

Into a 1-L-flask were added 692 mL of 13-HPOT/D at >80 g $L^{-1}$, 1.5 mL of 1 M of $MgSO_4$, 155 mL of isopropanol, 20 mL of 25 mM of NADP, 46 mL of the ketoreductase ADH 005 (775 U $mL^{-1}$) of Codexis (Redwood City, California) and 97 mL of lysed cells of *E. coli* containing the modified 13-HPL of the variant GC #7 (cell suspension equivalent to $OD_{600}$=7). The reaction was agitated with a magnetic stirrer at 800 rpm at room temperature for 40 min. Aliquots of 200 μL were withdrawn after 2, 5, 10, 20 and 40 min to monitor the reaction via gas chromatography. The entire reaction was then extracted 3× with MTBE. The organic extract was washed with water, dried over $Na_2SO_4$ and filtered with a PTFE membrane of 0.45 μm pore size prior to removal of the organic solvent by evaporation. The residue was then distilled using a standard distillation apparatus at 70-85° C. under vacuum (15 mbar). The purity of the (Z)-3-hexenol isolated was 97.8% with 1.2% of 1-hexanol, and 0.6% of (E)-2-hexenol as the main impurities (FIG. 3). The identity of the products was further verified by GC-MS and NMR.

Example 6

Synthesis of 9-HPOT/D

The 9-hydroperoxide of alpha-linolenic acid was prepared as follows: A multi-necked glass flask equipped with a mechanical stirrer, a thermometer, a dropping funnel, a glass cap and an oxygen inlet and a vacuum outlet was used. 370 g of freshly mashed potatoes (Charlotte or Bintje) were added to the multi-necked-glass flask. Then 30 g of linseed oil hydrolysate together with 250 gram of water containing 250 μL of Tween 80 (Sigma Aldrich, P4780), and 370 μL Viscozym L (Novozymes) were rapidly added. The temperature was adjusted to 20° C.-22° C. and the pH was kept at 5.5 to 5.7 by adding 30% of aqueous NaOH. The system was purged four times with oxygen, vigorously stirred at 800 rpm and kept under oxygen for 1 hour. The oxygen consumption was measured with the help of a burette. The fatty acid hydroperoxide concentration was determined by iodometric titration with 0.01 N of $Na_2S_2O_3$. The total 9-HPOT/D content (9-hydroperoxy-trienoic acid/9-hydroperoxydienoic acid) should be at least 30 g $L^{-1}$.

Example 7

Production of Crude 9-Hydroperoxide Lyase (9-HPL)

1 mL of an overnight culture of cells of *E. coli* DH5a harboring a recombinant expression plasmid based on pMAL-c-2X (New England Biolabs, Ipswich, MA) with the codon modified ORF of the 9-hpl (see e.g. U.S. Pat. No. 7,037,693B2) fused in frame to the 3' end of malE was added to a flask with 200 mL of sterile LB medium containing 100 mg mL-1 of ampicillin and 2 mg $L^{-1}$ of thiamine. Cells were grown under shaking at 220 rpm at 37° C. till an optical density of $OD_{600}$ of 0.5 was reached. Then 200 microL of 1M of 5-amino-levulinic acid were added to give a final concentration of 1 mM. The temperature was lowered to 25° C. and the culture induced with 0.1 mM of IPTG at an $OD_{600}$ of 0.6. The culture was then grown at 180 rpm at 25° C. for another 16 h. Cells were centrifuged at 4° C. and at 4000 g for 30 min. The supernatant was discarded and the cell pellet suspended in ice cold 100 mM phosphate buffer pH 7.6 to reach an $OD_{600}$ of 45. Lysozyme was added at 2 mg $L^{-1}$ and incubated on ice for 30 min prior to cell disruption by sonication using the LabsonicP (Sartorius, Gattingen, Germany).

Example 8

Sequential Cleavage of 9-HPOT/D and Chemical Reduction of the Aldehydes 900 microL of 9-HPOT/D at 35 g $L^{-1}$ of total peroxides were added to a glass vial. Then 100 microL of the crude 9-HPL were added under magnetic stirring. Samples of 100 microL were removed after 5 min, 10 min, 15 min and 20 min and immediately reduced in 900 microL of aqueous $NaBH_4$ of 10 g $L^{-1}$ under magnetic stirring at room temperature for 10 min. The reduced samples were extracted with 2 mL of MTBE containing 1-octanol as the internal standard and analyzed by GC using a DB-WAX column. After 5 minutes 0.2 g $L^{-1}$ of (Z)-3-nonenol and 0.9 g $L^{-1}$ of (Z,Z)-3,6-nonadienol were detected (Table 1).

TABLE 1

| Time (min) | (Z)-3-nonenol (g $L^{-1}$) | (Z,Z)-3,6-nonadienol (g $L^{-1}$) | Total (g $L^{-1}$) |
|---|---|---|---|
| 5 | 0.20 | 0.90 ± 0.01 | 1.11 ± 0.01 |
| 10 | 0.21 ± 0.01 | 0.92 ± 0.06 | 1.14 ± 0.08 |
| 15 | 0.20 ± 0.01 | 0.86 ± 0.04 | 1.06 ± 0.05 |
| 20 | 0.18 ± 0.06 | 0.80 ± 0.02 | 0.99 0.03 |

Example 9

Sequential Cleavage of 9-HPOT/D and Biochemical Reduction of the Aldehydes 1800 microL of 9-HPOT/D of 35 g $L^{-1}$ were added to a glass vial. Then 200 microL of the crude 9-HPL were added under magnetic stirring. The reaction was left under magnetic stirring at 900 rpm at room temperature for 5 min. Two samples of 100 microL each were removed as controls, reduced with $NaBH_4$ and analyzed as described. To the remainder of the reaction were immediately added: 120 microL of an aqueous 10 mM NADP, 160 microL $H_2O$, 70 microL of isopropanol, 11 microL of 1M $MgSO_4$, and 100 microL of the ketoreductase ADH005 (775 U $mL^{-1}$) of Codexis (Redwood City, California). The pH was adjusted to pH 7 by adding 12 microL of 20% NaOH under strong magnetic stirring. Samples of 200 microL were removed at different time intervals, extracted with 15 volumes of MTBE and analyzed by GC as described using 1-octanol as the internal standard. The biochemical reduction resulted in 0.13 g $L^{-1}$ of (Z)-3-nonenol and 0.59 g $L^{-1}$ of (Z,Z)-3,6-nonadienol with no free aldheydes detected after 5 minutes.

Example 10

Concomitant Cleavage of 9-HPOT/D and Reduction of the Aldehydes 1620 microL of 9-HPOT/D of 35 g $L^{-1}$ were added to a glass vial. Then 120 microL of 10 mM NADP, 160 microL of $H_2O$, 70 microL of isopropanol, 11 microL of 1M $MgSO_4$, 100 microL of the ketoreductase ADH005 of (775 U $mL^{-1}$) of Codexis (Redwood City, California), 180 microL of crude 9-HPL ($OD_{600}$=45) and 12 microL of 20% NaOH were added under stirring at room temperature (final pH=7). Samples of 200 microL were removed at different time intervals, extracted with 15 volumes of MTBE and analyzed by GC as described using 1-octanol as the internal standard. The biochemical reduction resulted in 0.16 g $L^{-1}$ of (Z)-3-nonenol and 0.68 g $L^{-1}$ of (Z,Z)-3,6-nonadienol with no free aldheydes detected after 5 minutes of reduction time.

Example 11

Concomitant Cleavage of 9-HPOT/D and Reduction of the Aldehydes 1620 microL of 9-HPOT/D of 35 g $L^{-1}$ were added to a glass vial. Then 40 microL of 10 mM NAD, 160 microL of $H_2O$, 70 microL of isopropanol, 200 microL of the ketoreductase IEPOx58 of Cambrex-IEP (Wiesbaden, Germany), 180 microL of crude 9-HPL ($OD_{600}$=45) and 12 microL of 20% NaOH were added under stirring at room temperature (final pH=7). Samples of 200 microL were removed at different time intervals, extracted with 15 volumes of MTBE and analyzed by GC as described using 1-octanol as the internal standard. The biochemical reduction resulted in 0.16 g $L^{-1}$ of (Z)-3-nonenol and 0.74 g $L^{-1}$ of (Z,Z)-3,6-nonadienol with no free aldheydes detected after 15 minutes of reduction time.

What is claimed is:

1. A composition comprising (Z,Z)-3,6-nonadienol, wherein the composition is produced by a method comprising:

a) contacting a 9-hydroperoxide of a polyunsaturated fatty acid selected from the group consisting of linoleic acid and alpha linolenic acid with a 9-hydroperoxide lyase to form an aldehyde selected from the group consisting of a nonenal and nonadienal; and b) reducing the aldehyde in the presence of a hydride donor, a ketoreductase, and a co-factor;

wherein the contacting and reducing steps are carried out concomitantly;

wherein the hydride donor is selected from the group consisting of a secondary alcohol, a primary alcohol, an alkandiol and a hydroxy acid or one of its esters;

the cofactor is selected from the group consisting of NADH and NADPH;

the hydroperoxide lyase is stable in the presence of the hydride donor, thus allowing for the concomitant hydroperoxide cleavage and aldehyde reduction; and the method is performed in the absence of intact cells;

wherein the composition comprises (Z,Z)-3,6-nonadienol in an amount greater than or equal to 0.74 g/l, and wherein the composition may comprise less than or equal to 1 g/l (Z)-3-nonenol.

2. The composition as recited in claim 1, wherein the ratio of (Z,Z)-3,6-nonadienol to (Z)-3-nonenol ranges from 4.63 up to 25:1.

3. A composition comprising an alcohol, wherein the composition is produced by a method comprising:

a) contacting a 9- or 13-hydroperoxide of a polyunsaturated fatty acid selected from the group consisting of linoleic acid and alpha linolenic acid with the respective hydroperoxide lyase to form an aldehyde; and b) reducing the aldehyde to form the alcohol in the presence of a hydride donor, a ketoreductase, and a co-factor wherein the contacting and reducing steps are carried out concomitantly;

wherein the hydride donor is selected from the group consisting of a secondary alcohol, a primary alcohol, an alkandiol and a hydroxy acid or one of its esters;

the cofactor is selected from the group consisting of NADH and NADPH;

the hydroperoxide lyase is stable in the presence of the hydride donor, thus allowing for the concomitant hydroperoxide cleavage and aldehyde reduction; and the method is performed in the absence of intact cells.

4. The composition of claim 3, wherein the composition comprises no (Z)-3-nonenol.

5. The composition of claim 3, wherein the composition comprises (Z,Z)-3,6-nonadienol in an amount greater than or equal to 4 g/l, and wherein the composition may comprise less than or equal to 0.16 g/l (Z)-3-nonenol.

* * * * *